US008012429B2

(12) United States Patent
Okauchi et al.

(10) Patent No.: US 8,012,429 B2
(45) Date of Patent: Sep. 6, 2011

(54) SIMPLIFIED ANALYZER

(75) Inventors: Kanji Okauchi, Tokyo (JP); Takao Kawarabayashi, Tokyo (JP)

(73) Assignee: Kyoritsu Chemical-Check Lab., Corp., Tokyo (JP)

( * ) Notice: Subject to any disclaimer, the term of this patent is extended or adjusted under 35 U.S.C. 154(b) by 1245 days.

(21) Appl. No.: 10/476,699

(22) PCT Filed: May 1, 2002

(86) PCT No.: PCT/JP02/04351
§ 371 (c)(1),
(2), (4) Date: Nov. 5, 2003

(87) PCT Pub. No.: WO02/090973
PCT Pub. Date: Nov. 14, 2002

(65) Prior Publication Data
US 2004/0136867 A1 Jul. 15, 2004

(30) Foreign Application Priority Data
May 7, 2001 (JP) ................................ 2001-136538

(51) Int. Cl.
*G01N 33/48* (2006.01)

(52) U.S. Cl. ........ 422/405; 422/401; 422/402; 422/430; 422/501; 422/570; 436/165; 73/863; 73/864

(58) Field of Classification Search ................. 422/68.1, 422/401, 402, 405, 430, 501, 570; 436/164, 436/165; 73/863, 864
See application file for complete search history.

(56) References Cited

U.S. PATENT DOCUMENTS 4,078,892 A * 3/1978 Steinbrink, Jr. ................ 436/97
4,409,182 A 10/1983 Macklem
4,522,640 A 6/1985 Jagoe, III
4,588,554 A 5/1986 Kaartinen et al.
(Continued)

FOREIGN PATENT DOCUMENTS

JP 58-193461 11/1983
(Continued)

OTHER PUBLICATIONS

"Collection note for utilizing patents owned by companies" (Jan. 2002), pp. 138-139 with first cover page, compiled by Intellectual Property Support Section, Technical Research Division, Japanese Patent Office.

(Continued)

*Primary Examiner* — Lyle Alexander
(74) *Attorney, Agent, or Firm* — Frommer Lawrence & Haug LLP

(57) ABSTRACT

There is provided a simplified analyzer including a see-through hermetic container having powdery or granular color reaction reagent, and a tap member partially inserted in the hermetic container in an extractable state. The tap member is provided at one end with a finger stopper larger in diameter than another portion, so as to be drawn out while holding the finger stopper with user's fingers to form a through hole for letting air out of the hermetic container and applying suction to the testing liquid to be analyzed. By using the tap member prepared in advance, the through hole having a suitable diameter for applying suction to the testing liquid to be analyzed can be formed at the appropriate point in the container. According to the analyzer of the invention, differences among individuals in performing an analyzing test do not occur.

54 Claims, 11 Drawing Sheets

U.S. PATENT DOCUMENTS 4,826,759 A * 5/1989 Guire et al. ........................ 435/4

FOREIGN PATENT DOCUMENTS

| | | |
|---|---|---|
| JP | 60-169571 | 9/1985 |
| JP | 60-169751 | 9/1985 |
| JP | 61-161758 | 7/1986 |
| JP | 2-168158 | 6/1990 |
| JP | 3-17562 | 2/1991 |
| JP | 2000-506419 | 5/2000 |

OTHER PUBLICATIONS

"Livelihood, human, life, and medical prescription for you; Alternative Thesis of Drug Induced Suffering: Part II" (Apr. 20, 1994), pp. 122-123 with first cover page, published by Jiho, Inc.

"Environmental Handbook: Practical Cases of Environmental Education Aiding in School Teaching" (First Edition, Second Printing in 1992), pp. 140-142, edited by Society for Study of Environmental Education for National Elementary and Junior High Schools and published by Japan Educational Press.

"Handbook for providing environmental education for senior high school, looking for livelihood and society good for environment" (Mar. 1994), pp. 36-38 with first cover page, published by Environmental Policy Section, Environmental Division, Osaka Prefectural Environment & Health Department.

Chinese Office Action dated Apr. 22, 2005 in counterpart Chinese Application No. 02809572.3 together with English translation thereof.

Notification of Reason for Rejection dated Mar. 6, 2007 in counterpart Japanese Patent Application No. 2002-588181 together with English translation thereof.

* cited by examiner

SIMPLIFIED ANALYZER

CROSS REFERENCES TO RELATED APPLICATIONS

This application is the U.S. National Stage of International Application No. PCT/JP02/04351, filed May 1, 2002.

BACKGROUND OF THE INVENTION

1. Field of the Invention

This invention relates to a simplified analyzer.

2. Description of the Related Art

In general, there have been broadly used an analytical test papers made by impregnating water absorbing paper with color reaction reagent for making a water quality analysis or the like. In order to analyze water quality by using a conventional simplified analyzer using the analytical test paper, the analysis of the water quality is carried out by soaking the analyzer in testing fluid to be analyzed, to react the testing fluid with the color reaction reagent and comparing the color of the testing fluid. The color of the testing fluid changes as the result of the reaction with the color reaction reagent and a standard color is prescribed as a reference color.

However, the conventional analyzer using the analytical test paper has a disadvantage in which it is inferior in sensitivity and accuracy of water quality analysis because the color reaction reagent may elute into the testing fluid when soaking the test paper in the testing fluid.

Correspondingly, there is known a simplified analyzer provided for improving the analyzing sensitivity as illustrated in FIG. 10. The conventional simplified analyzer 9 shown in FIG. 10 has a transparent or semitransparent hermetic container 90 containing powdered color reaction reagent 91. The hermetic container 90 may be made of a polyethylene tube having both ends sealed by thermal welding or ultrasonic welding or in another method.

In conducting a water quality analysis by use of the simplified analyzer, shown in FIGS. 10 and 11, it is necessary to thrust a pin 92, separately prepared, into the hermetic container 90 to make a small through hole 93 in the hermetic container 90. Then, as shown in FIG. 12, the air or gas 21 in the hermetic container 90 is let out of the container through the hole 93 by forcibly pinching the container 90 with fingers 20. Thereafter, the hermetic container 90 is soaked in the testing fluid 22 to allow the testing fluid 22 to flow into the hermetic container 90 like a dropper as shown in FIG. 13. Consequently, the color reaction reagent 91 and the testing fluid 22 are mixed inside the hermetic container 90 to cause the color reaction. After the lapse of predetermined time, the water quality analysis is concluded by comparing the color changed as the result of the color reaction, with a standard color to measure the concentration of the testing fluid.

The simplified analyzer described above has an advantage in that the color reaction reagent and the testing fluid to be analyzed can be increased in amount in comparison with the conventional analyzer using analytical test paper. Thus, this simplified analyzer makes it possible to analyze even dilute testing fluid and can prevent the color reaction reagent from eluting into the testing fluid, consequently to conduct the required water quality analysis with high accuracy.

Since the aforementioned simplified analyzer requires the pin for piercing the hermetic container to conduct the water quality analysis, it can be said that this conventional simplified analyzer aiming at the simplicity of the structure is incomplete without such an additional component, and therefore, it is desired to be further improved. Besides, since the hermetic container is manually pierced with the pin, some inexperienced workers may possibly pierce an awkward hole in the hermetic container, as the result of which it is possibly difficult to apply suction to the testing fluid sucked into a small hermetic container or deal with a relatively small amount of testing fluid.

The present invention is made in the light of the foregoing disadvantages of the conventional analyzer and seeks to provide a novel simplified analyzer capable of being handled easily and surely without using any other tool such as a pin and a method for producing the simplified analyzer.

BRIEF SUMMARY OF THE INVENTION

To attain the object described above according to the present invention, there is provided a simplified analyzer comprising a see-through hermetic container containing a reaction reagent, and a tap member piercing detachably through the aforesaid hermetic container.

When the analyzer is used, the tap member is removed from the hermetic container to let out the air of the container and suck test material to be analyzed into the container.

DETAILED DESCRIPTION OF THE INVENTION

Figure 1:
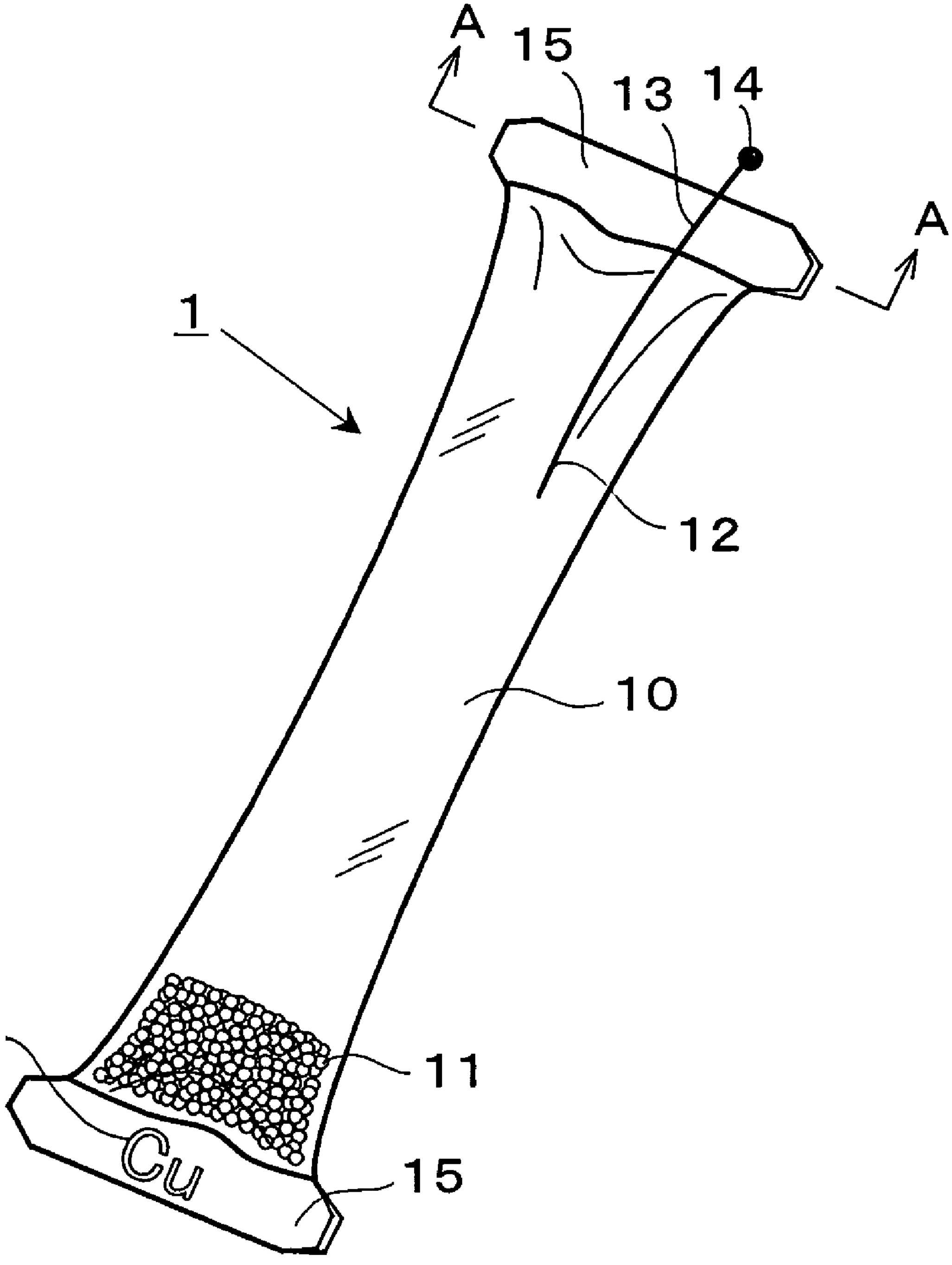
FIG. 1 is an explanatory diagram showing an embodiment of a simplified analyzer according to the present invention.

The simplified analyzer according to the present invention is characterized by a see-through hermetic container containing a reaction reagent, and a tap member piercing detachably through the aforesaid hermetic container.

According to this structure of the analyzer of the invention, only by removing the tap member from the hermetic container with fingers, the air is let out of the container, and alternatively, test material to be analyzed can be introduced into the container. The term "see-through" used herein for the hermetic container means that the container is wholly made transparent or semitransparent or a part of the container is made transparent or semitransparent, so that the content in the container can be visually checked.

Further, the simplified analyzer of the present invention is characterized by making the hermetic container of flexible plastic material.

With this structure, the hermetic container can be deformed by being depressed with a finger to let out the air of the container and suck testing fluid to be analyzed into the container.

The simplified analyzer of the invention has another feature that the hermetic container has seam portions formed by sealing the both end parts thereof by welding, and the tap member is embedded in one of the seam portions.

Consequently, the area of contact between the hermetic container and the tap member embedded in the hermetic container becomes wide to increase resistance to a force for pulling out the tap, consequently to prevent the tap member from falling off accidentally. As a result, the sealing performance of the hermetic container is elevated to prevent the reaction reagent and testing fluid from leaking.

The aforementioned simplified analyzer according to the invention has still another characteristic in that the tap member may be formed of a string or rod material.

This characteristic structure enables the tap member to be optimized in shape.

The present invention has a further characteristic in that the tap member is provided on its one end with a finger hook having a larger diameter than the other part.

Thus, the tap member can easily be removed from the container by hooking a finger through the finger hook and pulling. When the tap member once pulled out is inserted into the container, the finger hook is caught on a through hole formed in the seam portion of the container to prevent the tap member from being entirely inserted in the container by accident.

The aforementioned simplified analyzer according to the invention has a further feature in that the other tip end of the tap member is formed in an acuminate shape.

With the tap member having the acuminate tip end, even when the tap member is pulled out, it can easily be inserted in the seam portion of the container once again. The acuminate shape of the tap member may be formed by cutting the tip end of the tap member slantwise or tapering the tap member toward the tip end.

The aforementioned simplified analyzer according to the invention has a further feature in that one tip end of the tap member protrudes outward over the other tip end as viewed in the longitudinal direction.

The protrusion at one of the tip ends of the tap member brings about resistance to a force for pulling up the tap member so as to prevent the tap member from coming off accidentally.

The present invention has a further characteristic in that the hermetic container and the tap member in the simplified analyzer of the invention are formed in different colors.

By forming the hermetic container and the tap member in the simplified analyzer of the invention in different colors, the tap member can readily be discerned when being drawn out from the hermetic container, thus to facilitate the required analytical work.

The present invention has a further characteristic in that one or more of the simplified analyzers according to the invention may be packed as one unit in a moisture-proof wrapping.

The reaction reagent contained in the hermetic container of the simplified analyzer packed in the moisture-proof wrapping can be completely protected without being affected by moisture in the air or the like.

Another object of the present invention is to provide a method for producing the aforementioned simplified analyzer having a characteristic in that the hermetic container can readily be produced by preheating the edge portion of the container and thermally sealing the preheated edge portion by welding while keeping the tap member in the edge portion.

According to this method, the hermetic container can securely be sealed by welding without adhering to the tap member, so that the tap member can easily be pulled out.

One embodiment of the present invention will be described in detail hereinafter.

FIGS. 1 to 9 illustrate an embodiment of the simplified analyzer according to the present invention along with the processes of using the analyzer. In the illustrated embodiment, a color reaction reagent is used as a chemical agent for use in a reaction. Just as one example, the simplified analyzer described herein is applied for analyzing water quality.

The simplified analyzer 1 generally comprises the transparent or semitransparent hermetic container 10 containing the color reaction reagent 11 and the tap member 12 partially inserted in the hermetic container 10. The tap member 12 can be pulled out from the hermetic container 10 with a finger 20, consequently to form a through hole 13 in the hermetic container.

The hermetic container 10 is made transparent or semitransparent, so that the color of the reagent can be visually checked from the outside after causing a color reaction. The hermetic container 10 is preferably made of chemically stable synthetic resin such as polyethylene, polyethylene terephthalate, and nylon. The hermetic container 10 is made flexible so that it can be deformed by being depressed with a finger to let out air or gas 21 of the container or suck testing fluid 22 into the container.

The tap member 12 is formed of a string or rod material as shown in FIG. 1 for example and partly thrust in the hermetic container so as to be pulled out of the hermetic container 10. The string-shaped (or rod-shaped) tap member 12 has a length, which is not specifically limited, so as not to come off accidentally. The tap member 12 is preferably made of chemically stable and flexible synthetic resin such as polyethylene, polypropylene, and polyethylene terephthalate.

Figure 2:
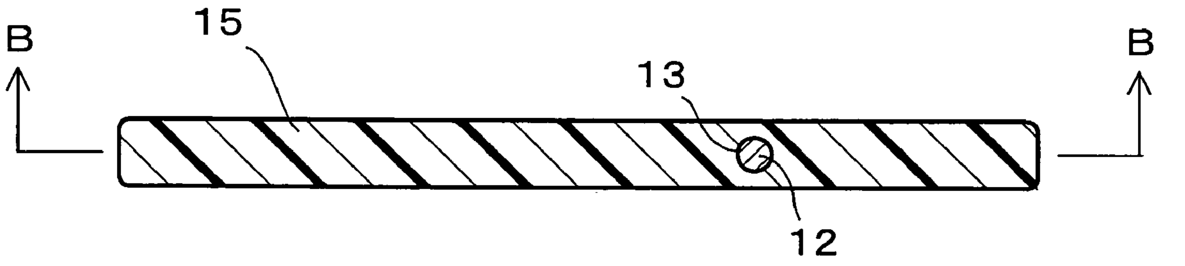
FIG. 2 is a cross sectional view taken along line A-A in FIG. 1.
Figure 3:
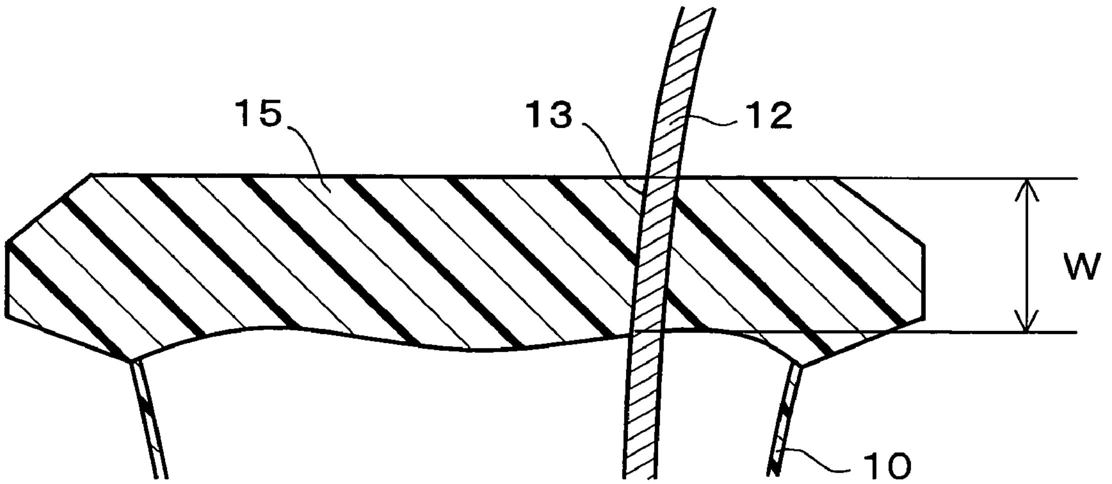
FIG. 3 is a cross sectional view taken along line B-B in FIG. 2.

On both end portions of the tube-like hermetic container 10, there are formed seam portions 15 formed by thermally sealing the end portions of the container. In one of the seam portions 15, the tap member 12 is partly embedded by the length corresponding to the width W of seam portion 15 as shown in FIG. 2 and FIG. 3. With this structure, the hermetic container 10 (seam portion 15) and the tap member 12 come in contact with each other with a large area, consequently fixing tap creating resistance to a force for pulling up the tap member so as to prevent the tap member from coming off (being removed) accidentally. As is clear from FIGS. 1-3, the tap member 12 extends entirely through the seam portion 15 to thereby extend from an exterior of hermetic container 10 to an interior of hermetic container 10. In addition, the sealing performance of the hermetic container is elevated to prevent the color reaction reagent 11 from leaking through the hole 13. Besides, even when the tap member 12 once pulled out is inserted into the container once again after sucking the testing fluid 22 into the container as described later, the testing fluid 22 sucked in the container can be prevented from leaking. The width W of the seam portion 15 is arbitrarily determined according to the size of the tap member 12 or other conditions.

Where the width of the seam portion is too large, the resistance to the force for pulling out the tap member is needlessly increased. To be more specific, it is preferable to determine the width W of the order of 3 to 4 mm.

In the embodiment in FIG. 1, the tap member 12 is provided on its one end with a finger hook 14 having a larger diameter than the other part. According to this structure, the tap member 12 can easily be removed from the container 10 by hooking a finger through the finger hook 14 and pulling. When the tap member 12 once pulled out is inserted into the container 10, the finger hook 14 is caught on a through hole formed in the seam portion of the container to prevent the tap member 12 from being entirely inserted in the container 12 by accident. The way of forming the finger hook 14 is not specifically limited. The finger hook of the tap member may be made in the form of a mold ball yielded as the result of molding, or otherwise, the finger hook 14 separately prepared may be attached later to the stem of the tap member 12 with adhesives. Thus, the finger hook may be formed in this or other possible ways.

The tap member 12 may be formed in a different color from that of the hermetic container 10. By coloring the tap member 12 in different color from that of the hermetic container 10, the tap member 12 is highly visible to be easily distinguishable from other components, thus to permit a tester to work faster without feeling stress. However, the present invention of course encompasses the simplified analyzer comprising the tap member 12 and the hermetic container 10 of the same color or uncolored.

The hermetic container 10 may be provided with an analyzing data display 16. The analyzing data display 16 indicates helpful information such as the content name (testing material "Cu" in FIG. 1 by way of example), representation of the limit value of analysis or other information. The information displayed may be marked by printing, embossing or other measures.

The tap member 12 can be inserted in the hermetic container 10 in the state of capable of being pulled out by the following method. That is, the tap member 12 may be set in the hermetic container by preheating the edge portion of the hermetic container 10 made of synthetic resin at temperatures above the melting point of Tg, and then, thermally sealing the preheated edge portion by welding while keeping the tap member 12 in the edge portion. Thus, the seam portion 15 is formed at the edge portion of the hermetic container 10 by thermally sealing to firmly seal the hermetic container, but the tap member 12 and the seam portion 15 never melt together so as to be separatable by pulling the tap member 12. This is because the melting of the seam portion 15 is terminated before the tap member 12 reaches its melting point, although the tap member 12 is heated with the preheat applied to the hermetic container 10. Furthermore, the tap member 12 comes in close contact with the hermetic container 10, leaving no space therebetween, owing to the part in the molten state of hermetic container 10, which flows into between the tap member 12 and the inside wall of the through hole 13 in the process of melting the hermetic container 10, and by virtue of the elastic force brought about by the tap member 12 and hermetic container 10. As a result, the simplified analyzer of the invention never leaks the color reaction agent 11 and the testing fluid 22 even when the tap member 12 is once pulled out and again inserted therein upon sucking the testing fluid 22, as described later.

The melting points of the hermetic container 10 and the tap member 12 are not specifically limited, but it is preferable to use the hermetic container 10 and the tap member 12 having the same melting point or tap member 12 having a higher melting point than the hermetic container 10 to prevent the hermetic container 10 and the tap member 12 from being completely molten together. Thus, it is desirable to choose the materials of the hermetic container 10 and the tap member 12 so as to satisfy such conditions of the melting point. However, the present invention does not at all exclude use of the tap member 12 having a melting point lower than that of the hermetic container 10. In the case of using the tap member 12 having the lower melting point, the hermetic container 10 and the tap member 12 can be certainly prevented from being melted together by controlling the melting conditions such as a pressure to be applied to the hermetic container 10 and the tap member 12.

Figure 7:
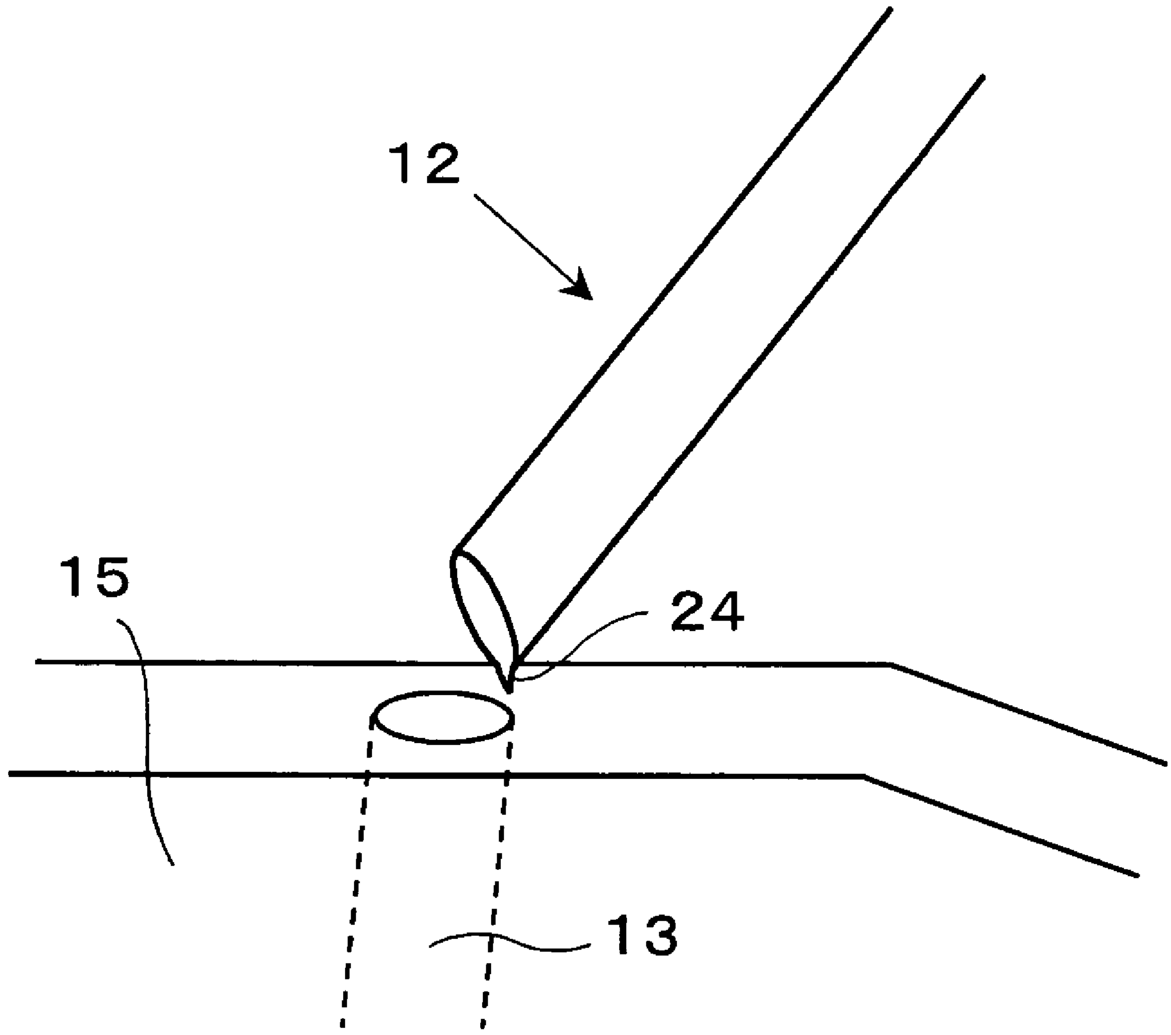
FIG. 7 is an enlarged view showing a tap member used in the analyzer.

The tap member 12 can be pulled out, hooking a finger through the finger hook 14 of the tap member 12. However, if the resistance brought about in pulling out the tap member 12 is a little more than necessary, it remains possible that the tap member 12 comes off accidentally. In such a case, the surface of the tap member 12 may be knurled so as not to come off with ease. Thus, the resistance to the force for pulling off the tap member 12 can be arbitrarily regulated. Moreover, one tip end of the tap member 12 (one of the tip ends of the tap member 12, from which the tap member 12 is inserted into the hermetic container 10) protrudes outward over the other tip end as viewed in the longitudinal direction, to form a protrusion 24, as shown in FIG. 7. With this protrusion 24, resistance to a force for pulling out the tap member 12 is brought about around the through hole 13 so as to prevent the tap member 12 from coming off accidentally with ease. The protrusion 24 may be formed separately from the tap member 12 by molding or integrally with the tap member 12 by using burr left in the process of molding the tap member 12. The protrusion 24 may be suitably shaped according to need. It is a matter of course that the present invention encompasses the tap member having no protrusion 24.

Figure 4:
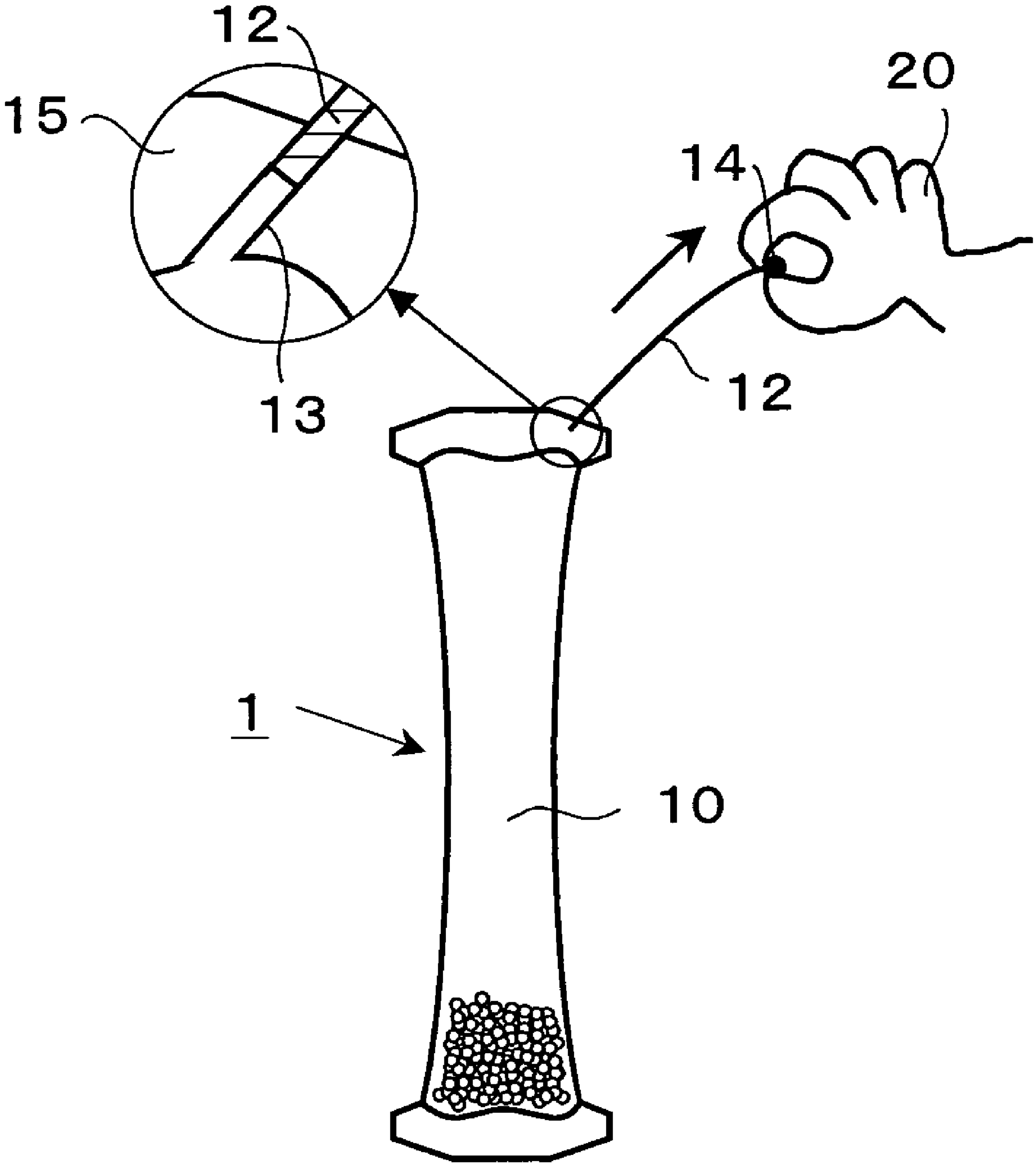
FIG. 4 is an explanatory diagram illustrative of the procedure for using the simplified analyzer according to the present invention.
Figure 5:
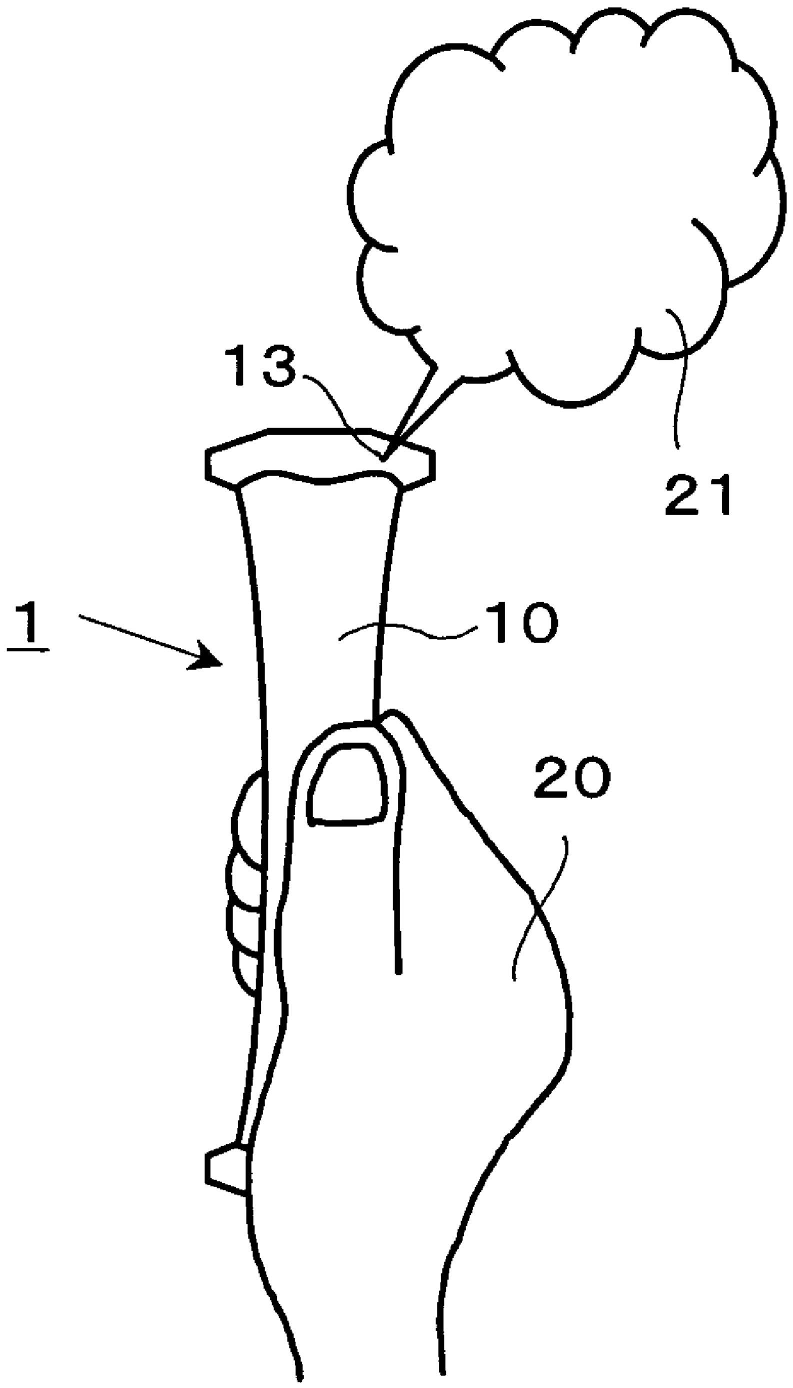
FIG. 5 is an explanatory diagram illustrative of the procedure for using the simplified analyzer according to the present invention.
Figure 6:
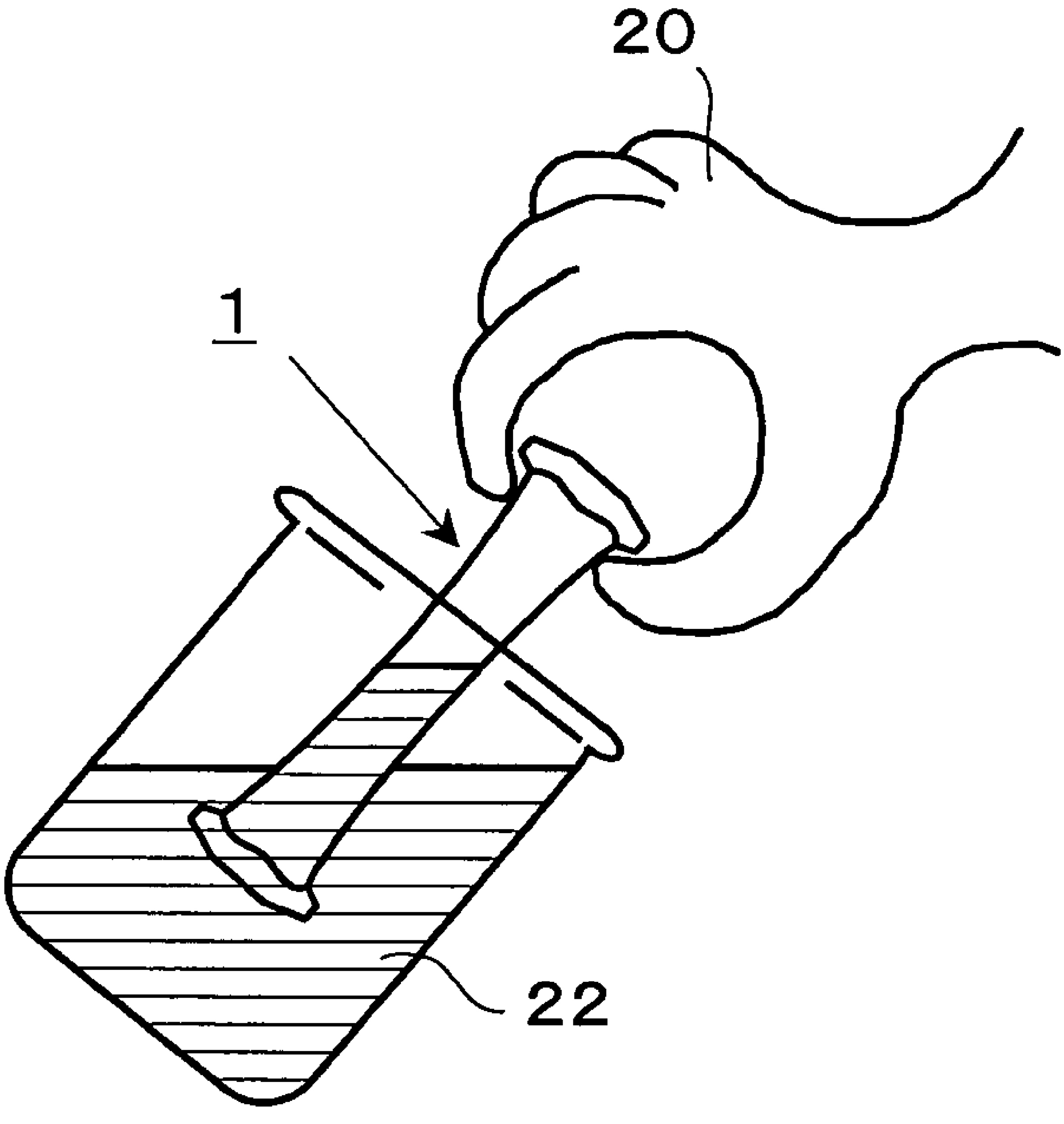
FIG. 6 is an explanatory diagram illustrative of the procedure for using the simplified analyzer according to the present invention.

The simplified analyzer 1 described above is handled in use by first pulling out the tap member 12 to make the through hole 13 as shown in FIG. 4, and then, pushing the hermetic container 10 with a finger 20 to extrude the air or other gas 21 out of the hermetic container 10 through the through hole 13 as shown in FIG. 5. Next, the simplified analyzer is soaked in the testing fluid 22 to be analyzed, placing the through hole 13 under the testing fluid, and then, the finger 20 is released from the hermetic container 10 to suck the testing fluid 22 into the hermetic container 10. Subsequently, upon shaking the hermetic container 10 if necessary, after the lapse of the prescribed time, the color of the fluid reacted with the color reaction reagent is compared with a standard color prepared separately as a reference color to determine the concentration of the testing fluid.

After sucking the testing fluid 22 into the hermetic container 10 in performing the aforesaid water quality analysis, the tap member 12 once pulled out is again inserted into the through hole 13 to prevent the testing fluid 22 from leaking from the hermetic container. The reason why the testing fluid 22 can be prevented from leaking out is uncertain, but it is more than probable that it is because the tap member 12 inserted into the through hole comes in tight contact with the inner wall of the through hole 12 in the seam portion 15 with elasticities of the tap member and seam portion, and the surface tension of the testing fluid 22 is not as low as the fluid leaks out. Since the testing fluid 22 does not leak, the problems such that the leaked liquid may stain clothes and influence the human body harmfully can be eliminated.

The other tip end of the tap member 12 (the tip end from which the tap member 12 is inserted into the hermetic container 10) may be formed in an acuminate shape if desired.

The acuminate shape of the tap member may be formed by cutting the tip end of the tap member slantwise or tapering the tap member toward the tip end as shown in FIG. 7. With the tap member having the acuminate tip end, even when the tap member 12 is pulled out, it can easily be inserted into the through hole 13 once again. The method for forming the acuminate shape of the tap member is not specifically limited, but it is better to cut the tip end of the tap member 12 slantwise to form the acuminate shape. It is a matter of course that the present invention encompasses the tap member having its tip end cut orthogonally to the longitudinal direction.

As an alternative, another tap member prepared separately may be inserted into the through hole 13 in place of the tap member 12 pulled out from the hermetic container to prevent the testing fluid from leaking out. In this case, the tap member 12 prepared separately may be tapered toward the tip end so as to be easily inserted into the through hole 13.

Figure 8:
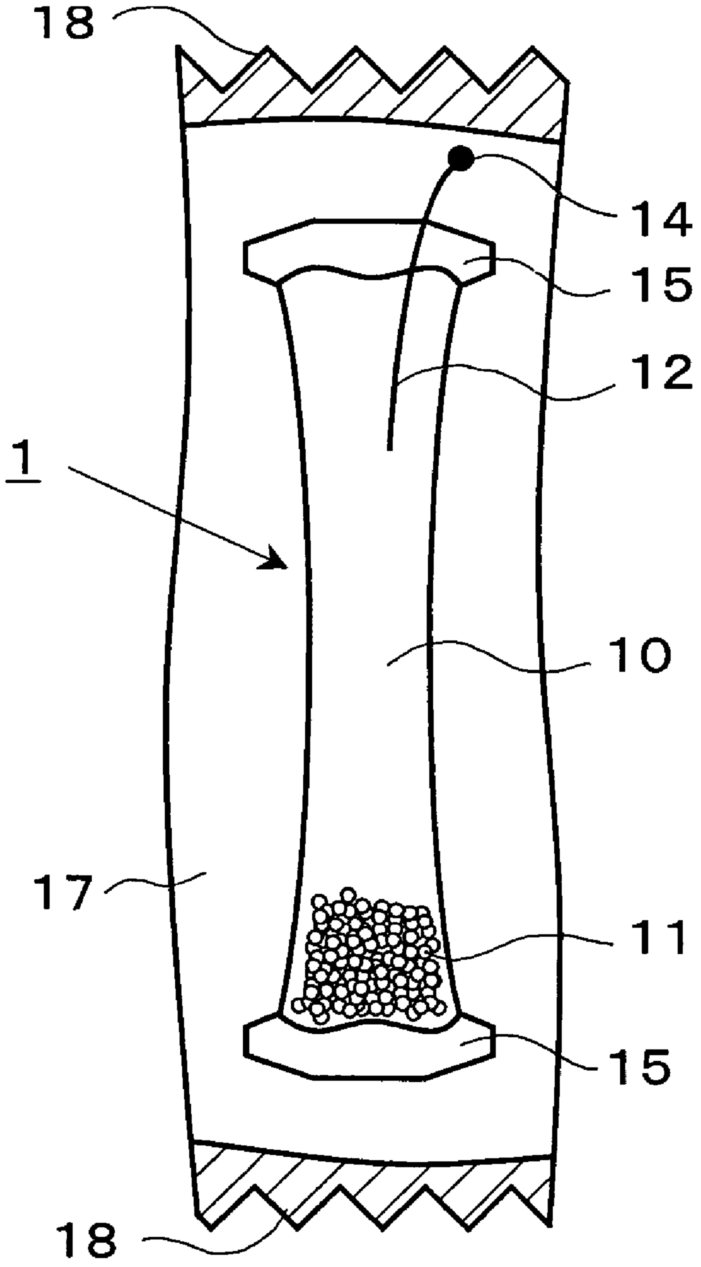
FIG. 8 is a view showing the simplified analyzer in its wrapped state according to the present invention.
Figure 9:
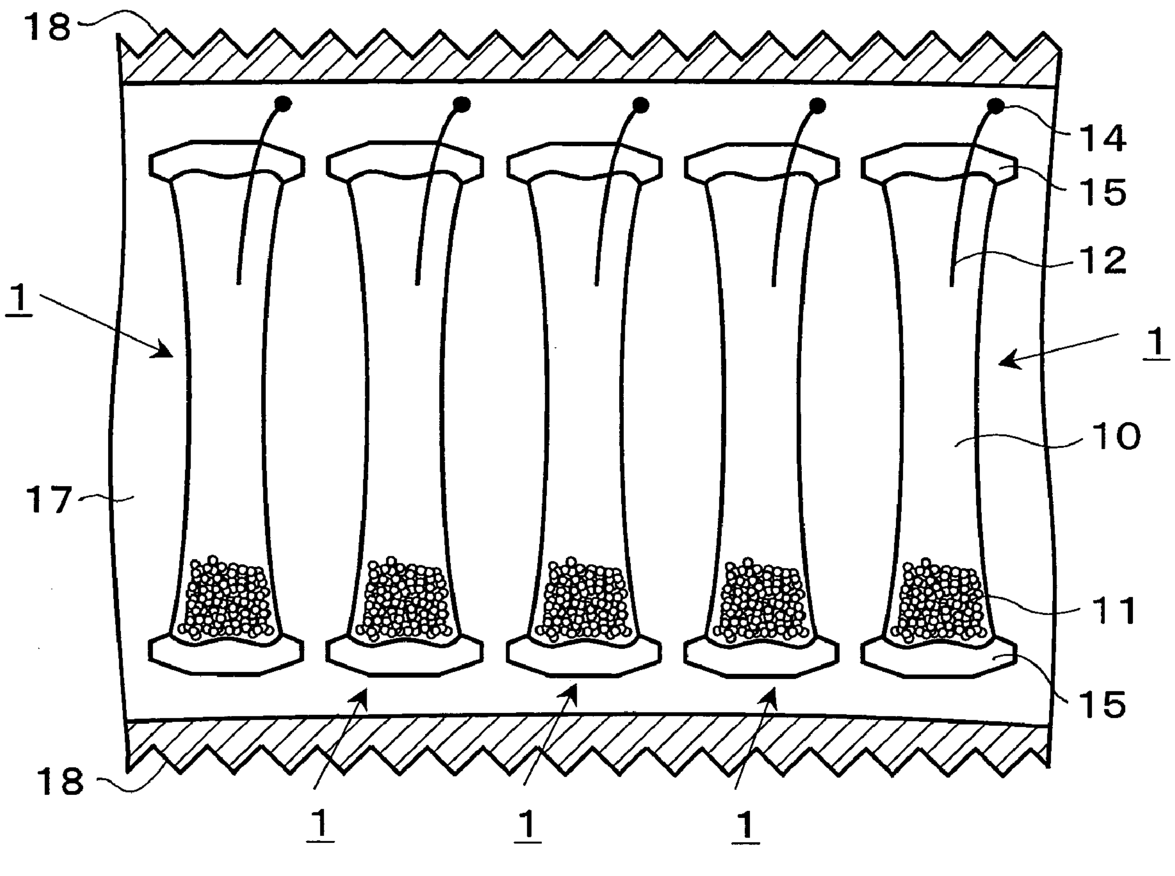
FIG. 9 is a view showing the simplified analyzer in its wrapped state according to the present invention.
Figure 10:
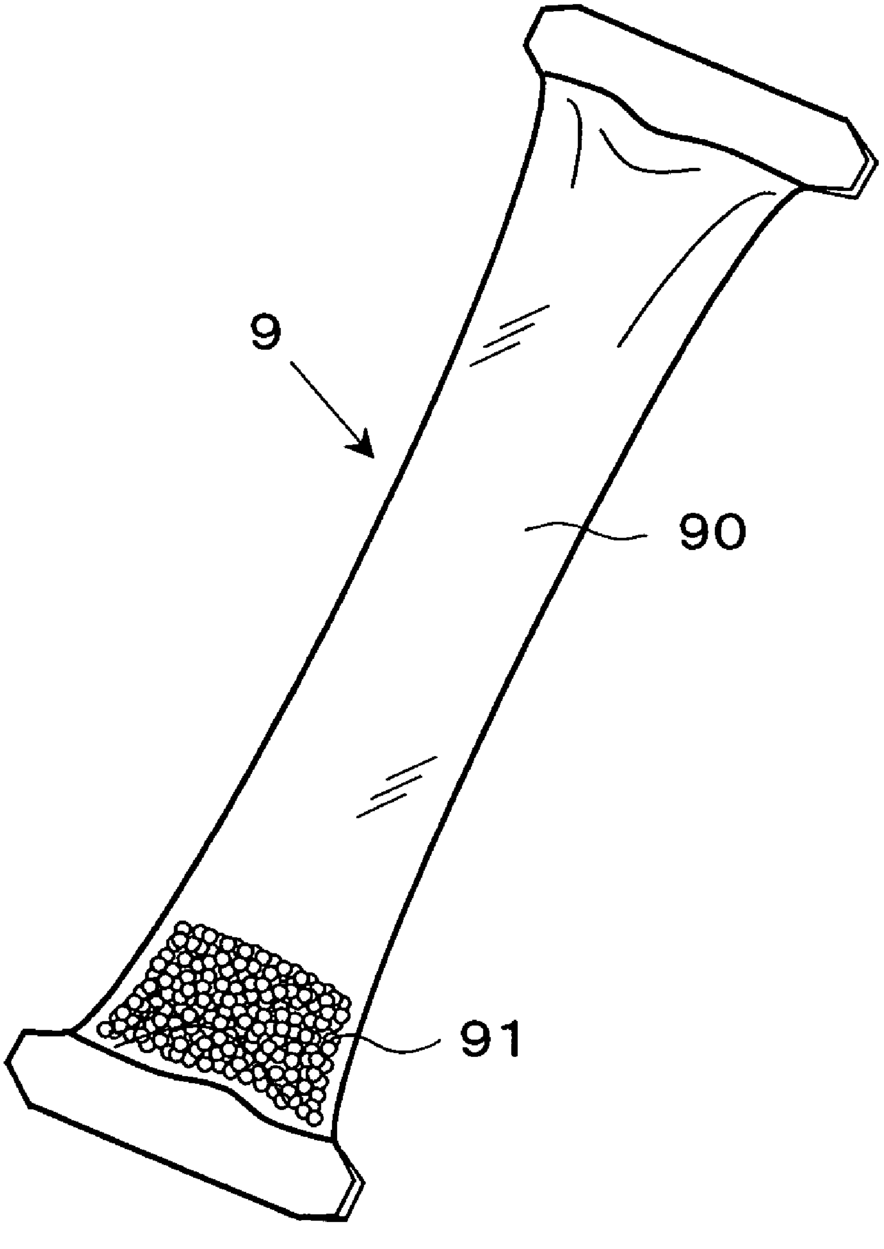
FIG. 10 is a view showing a conventional simplified analyzer.
Figure 11:
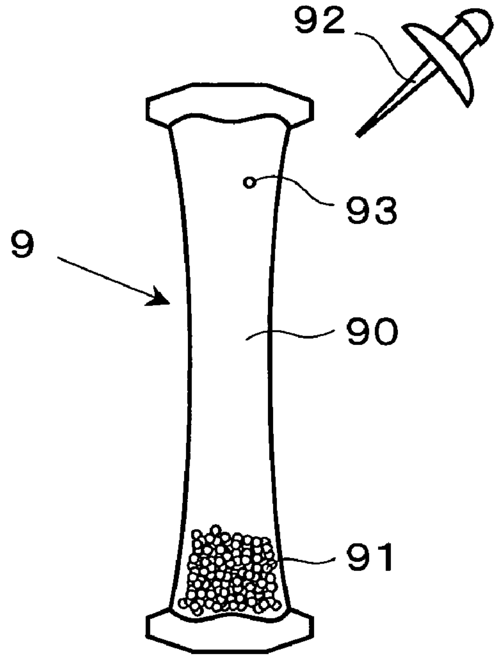
FIG. 11 is a diagram illustrative of the procedure for using the conventional simplified analyzer.
Figure 12:
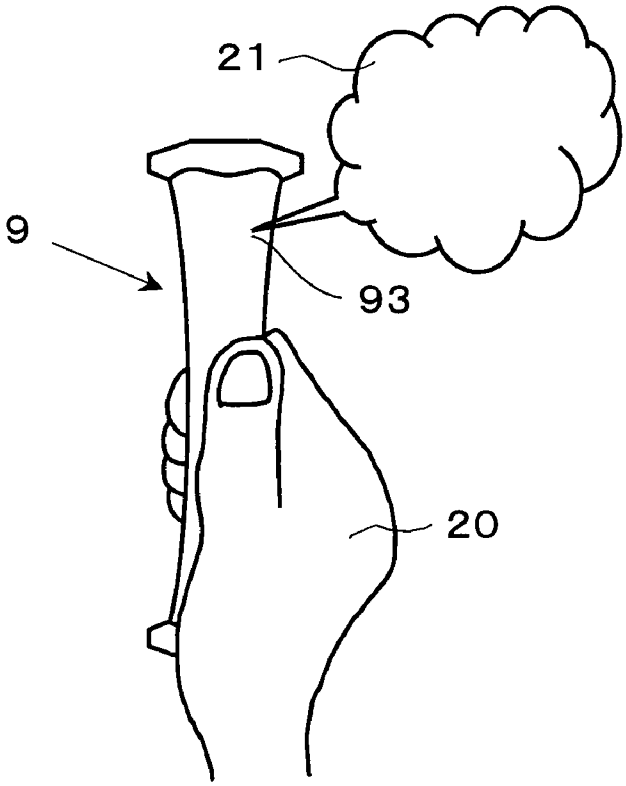
FIG. 12 is a diagram illustrative of the procedure for using the conventional simplified analyzer.
Figure 13:
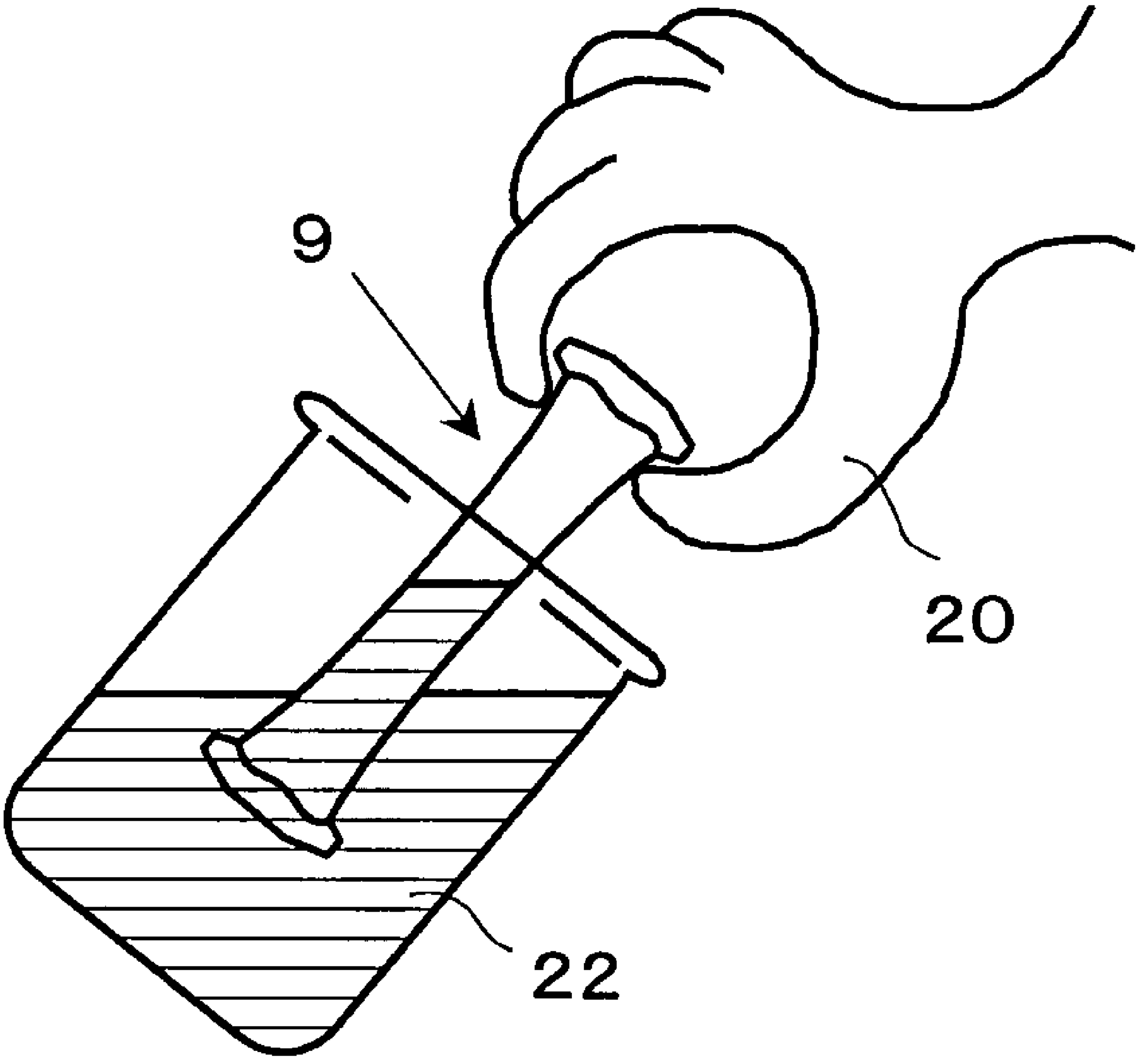
FIG. 13 is a diagram illustrative of the procedure for using the conventional simplified analyzer.

The aforementioned simplified analyzer 1 may be packed with a moisture-proof wrapping 17 as shown in FIG. 8 and FIG. 9. Thus, even when higher moisture-proofing property is required for the hermetic container 10 and the tap member 12, deterioration and deliquescence of the color reaction reagent 11 can assuredly be prevented. The moisture-proof wrapping 17 may be formed of synthetic resin sheet, synthetic resin sheet laminated with metallic foil, or the like. In packing the simplified analyzer 1, a drying agent, though not shown in the accompanying drawings, may be contained in the wrapping together with the simplified analyzer 1 if required. The method for packing the simplified analyzer 1 in the wrapping is not specifically limited, but it may be cited that the simplified analyzer 1 can be packed by being contained with the tube-like wrapping 17 made of film or sheet and sealing the both ends of the tube-like wrapping by thermal welding or ultrasonic welding.

FIG. 8 illustrates one simplified analyzer 1 packed in the wrapping, and FIG. 9 illustrates five simplified analyzers packed in the wrapping by way of example. Thus, the number of simplified analyzers packed is not specifically limited. As shown in FIG. 8 and FIG. 9, a V-cut 18 may be formed in one edge portion of the moisture-proof wrapping 17 so as to make it easier to take out the simplified analyzer 1 from the wrapping by tearing the wrapping from the V-cut 18.

In the embodiment described above, the color reaction reagent 11 is sealed in the container by way of example, but any fluid or material visible from the outside of the container may be contained therein. As one example, a reaction reagent for precipitation may be used.

Furthermore, the aforementioned embodiment includes the hermetic container 10 made transparent or semitransparent in its entirety, but the hermetic container 10 may be made transparent or semitransparent in part as long as the contents in the container can be visibly checked from the outside.

Only the manner of using the simplified analyzer 1 for making an analysis of water quality was described above, but the simplified analyzer of the invention may be applied for gas detection or the like.

As is apparent from the foregoing disclosure, the simplified analyzer 1 according to the present invention can easily be handled in safety by anyone only by pulling out the tap member 12 to let out the air of the hermetic container 10 and suck the testing fluid into the hermetic container 10 without using any separate tool such as a pin. Furthermore, since the simplified analyzer 1 of the invention intrinsically has the tap member 12, the through hole 13 having a desirable diameter can be made at a suitable position of the hermetic container 10 for sucking the testing fluid into the container 10, consequently to eliminate differences between individuals in conducting various kinds of analyses and enhance the reliability of analysis.

The invention claimed is:

1. A simplified analyzer comprising:

a see-through hermetic container containing a reaction reagent, said hermetic container comprising two end parts each having a hermetic container seam portion; and a solid elongated tap member made of flexible resin, said tap member being detachably embedded in said seam portion of one of said end parts so as to extend entirely through said seam portion to extend from an exterior of said hermetic container to an interior of said hermetic container, said tap member being detachably embedded within said seam portion so as to form a through-hole through said seam portion when pulled out of said seam portion.

2. The simplified analyzer set forth in claim 1, wherein said hermetic container is formed from a flexible plastic material.

3. The simplified analyzer set forth in claim 1, wherein said elongated tap member comprises a string or rod formed from a synthetic resin.

4. The simplified analyzer set forth in claim 1, wherein said elongated tap member comprises a body and a finger hook at an end thereof, wherein said finger hook has a diameter greater than a diameter of said body.

5. The simplified analyzer set forth in claim 3, wherein said elongated tap member further comprises a body and a finger hook at an end thereof, wherein said finger hook has a diameter greater than a diameter of said body.

6. The simplified analyzer set forth in claim 3, wherein said elongated tap member further comprises a body and a finger hook at an end thereof, wherein said finger hook has a diameter greater than a diameter of said body; and an other end of said elongated tap member is formed in an acuminate shape.

7. The simplified analyzer set forth in claim 5, wherein an other end of said elongated tap member is formed in an acuminate shape and said hermetic container is formed from a flexible plastic material.

8. The simplified analyzer set forth in claim 3, wherein an end of said elongated tap member has a tip that includes a first side that protrudes further in a longitudinal direction of said elongated tap member than a second side of said tip opposite said first side.

9. The simplified analyzer set forth in claim 5, wherein an end of said elongated tap member has a tip that includes a first side that protrudes further in a longitudinal direction of said elongated tap member than a second side of said tip opposite said first side.

10. The simplified analyzer set forth in claim 6, wherein an end of said elongated tap member has a tip that includes a first side that protrudes further in a longitudinal direction of said elongated tap member than a second side of said tip opposite said first side.

11. The simplified analyzer set forth in claim 7, wherein an end of said elongated tap member has a tip that includes a first side that protrudes further in a longitudinal direction of said elongated tap member than a second side of said tip opposite said first side.

12. The simplified analyzer set forth in claim 1, wherein said hermetic container is a different color than said elongated tap member.

13. The simplified analyzer set forth in claim 3, wherein said hermetic container is a different color than said elongated tap member.

14. The simplified analyzer set forth in claim 4, wherein said hermetic container is a different color than said elongated tap member.

15. The simplified analyzer set forth in claim 5, wherein said hermetic container is a different color than said elongated tap member.

16. The simplified analyzer set forth in claim 6, wherein said hermetic container is a different color than said elongated tap member.

17. The simplified analyzer set forth in claim 7, wherein said hermetic container is a different color than said elongated tap member.

18. The simplified analyzer set forth in claim 8, wherein said hermetic container is a different color than said elongated tap member.

19. The simplified analyzer set forth in claim 9, wherein said hermetic container is a different color than said elongated tap member.

20. The simplified analyzer set forth in claim 10, wherein said hermetic container is a different color than said elongated tap member.

21. The simplified analyzer set forth in claim 11, wherein said hermetic container is a different color than said elongated tap member.

22. The simplified analyzer set forth in claim 1, wherein said analyzer is packed as one unit in a moisture-proof wrapping.

23. The simplified analyzer set forth in claim 3, wherein said analyzer is packed as one unit in a moisture-proof wrapping.

24. The simplified analyzer set forth in claim 4, wherein said analyzer is packed as one unit in a moisture-proof wrapping.

25. The simplified analyzer set forth in claim 5, wherein said analyzer is packed as one unit in a moisture-proof wrapping.

26. The simplified analyzer set forth in claim 6, wherein said analyzer is packed as one unit in a moisture-proof wrapping.

27. The simplified analyzer set forth in claim 7, wherein said analyzer is packed as one unit in a moisture-proof wrapping.

28. The simplified analyzer set forth in claim 8, wherein said analyzer is packed as one unit in a moisture-proof wrapping.

29. The simplified analyzer set forth in claim 9, wherein said analyzer is packed as one unit in a moisture-proof wrapping.

30. The simplified analyzer set forth in claim 10, wherein said analyzer is packed as one unit in a moisture-proof wrapping.

31. The simplified analyzer set forth in claim 11, wherein said analyzer is packed as one unit in a moisture-proof wrapping.

32. The simplified analyzer set forth in claim 12, wherein said analyzer is packed as one unit in a moisture-proof wrapping.

33. The simplified analyzer set forth in claim 13, wherein said analyzer is packed as one unit in a moisture-proof wrapping.

34. The simplified analyzer set forth in claim 14, wherein said analyzer is packed as one unit in a moisture-proof wrapping.

35. The simplified analyzer set forth in claim 15, wherein said analyzer is packed as one unit in a moisture-proof wrapping.

36. The simplified analyzer set forth in claim 16, wherein said analyzer is packed as one unit in a moisture-proof wrapping.

37. The simplified analyzer set forth in claim 17, wherein said analyzer is packed as one unit in a moisture-proof wrapping.

38. The simplified analyzer set forth in claim 18, wherein said analyzer is packed as one unit in a moisture-proof wrapping.

39. The simplified analyzer set forth in claim 19, wherein said analyzer is packed as one unit in a moisture-proof wrapping.

40. The simplified analyzer set forth in claim 20, wherein said analyzer is packed as one unit in a moisture-proof wrapping.

41. The simplified analyzer set forth in claim 21, wherein said analyzer is packed as one unit in a moisture-proof wrapping.

42. The simplified analyzer set forth in claim 2, wherein said elongated tap member comprises a string or rod formed of a synthetic resin.

43. The simplified analyzer set forth in claim 2, wherein said elongated tap member comprises a body and a finger hook at an end thereof, wherein said finger hook has a diameter greater than a diameter of said body.

44. The simplified analyzer set forth in claim 2, wherein said hermetic container is a different color than said elongated tap member.

45. The simplified analyzer set forth in claim 2, wherein said analyzer is packed as one unit in a moisture-proof wrapping.

46. The simplified analyzer set forth in claim 1, wherein said elongated tap member is intrinsically and detachably embedded in said seam portion of said one of said end parts.

47. A simplified analyzer comprising:

a see-through hermetic container containing a reaction reagent, said hermetic container comprising two end parts each having a hermetic container seam portion formed by sealing each of said two end parts by thermal welding, and a solid elongated tap member made of flexible resin, said tap member being detachably embedded in said scam portion of one of said end parts during the thermal welding so as to extend entirely through said seam portion to extend from an exterior of said hermetic container to an interior of said hermetic container.

48. The simplified analyzer set forth in claim 47, wherein said elongated tap member comprises a string or rod formed from a synthetic resin.

49. The simplified analyzer set forth in claim 47, wherein said elongated tap member comprises a body and a finger hook at an end thereof, wherein said finger hook has a diameter greater than a diameter of said body.

50. The simplified analyzer set forth in claim 47, wherein an end of said elongated tap member has a tip that includes a first side that protrudes further in a longitudinal direction of said elongated tap member than a second side of said tip opposite said first side.

51. The simplified analyzer set forth in claim 47, wherein said hermetic container is a different color than said elongated tap member.

52. The simplified analyzer set forth in claim 47, wherein said analyzer is packed as one unit in a moisture-proof wrapping.

53. The simplified analyzer set forth in claim 47, wherein said elongated tap member further comprises a body and a finger hook at a first end thereof, said finger hook having a diameter greater than a diameter of said body;

wherein a second end of said elongated tap member opposite said first end is formed in an acuminate shape; and wherein said hermetic container is formed from a flexible plastic material.

54. A simplified analyzer comprising:

a hermetic container containing a reaction reagent, said hermetic container having two end parts, each end part having a thermally welded seam portion, a solid elongated tap member made of a flexible resin, said tap member detachable embedded in one of the seam portions and extending from an exterior of said hermetic container through the entire seam portion and into an interior of said hermetic container; and a through-hole formed through the entire seam portion only when said tap member is initially detached from being embedded in said seam portion by being pulled-out of said seam portion.

* * * * *